(12) United States Patent
Yang (10) Patent No.: US 11,534,548 B2
(45) Date of Patent: Dec. 27, 2022

(54) SYSTEM AND METHOD FOR A CLOSED LOOP CONTROL IN AN ARTIFICIAL PANCREAS

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 214 days.

(21) Appl. No.: 16/471,569

(22) PCT Filed: Dec. 30, 2016

(86) PCT No.: PCT/CN2016/113690
§ 371 (c)(1),
(2) Date: Jun. 20, 2019

(87) PCT Pub. No.: WO2018/120104
PCT Pub. Date: Jul. 5, 2018

(65) Prior Publication Data
US 2019/0307958 A1    Oct. 10, 2019

(51) Int. Cl.
*A61M 5/172* (2006.01)
*G16H 40/63* (2018.01)
(Continued)

(52) U.S. Cl.
CPC ......... *A61M 5/1723* (2013.01); *A61B 5/0004* (2013.01); *A61B 5/0205* (2013.01); *A61B 5/1118* (2013.01); *A61B 5/14532* (2013.01); *A61B 5/4839* (2013.01); *A61B 5/6833* (2013.01); *A61M 5/14244* (2013.01);
(Continued)

(58) Field of Classification Search
CPC ............ A61M 5/1723; A61M 5/14248; A61M 2005/1726; G16H 40/63
See application file for complete search history.

(56) References Cited

U.S. PATENT DOCUMENTS

| 7,879,026 B2 * | 2/2011 | Estes ................. A61M 5/14244 604/890.1 |
| 8,152,789 B2 * | 4/2012 | Starkweather ......... G16H 50/30 604/504 |
| 8,257,300 B2 * | 9/2012 | Budiman ............. A61B 5/4839 604/66 |

(Continued)

FOREIGN PATENT DOCUMENTS

| CN | 103889317 | 6/2014 |
| CN | 106137214 | 11/2016 |

OTHER PUBLICATIONS

"International Search Report (Form PCT/ISA/210) of PCT/CN2016/113690," dated Oct. 10, 2017, pp. 1-2.

*Primary Examiner* — Laura A Bouchelle
(74) *Attorney, Agent, or Firm* — JCIP Global Inc.

(57) ABSTRACT

The present invention provides a closed loop control method in an artificial pancreas and a system using the method, comprising sensing an activity level of a patient by at least one motion sensor and providing signals to at least one processor; then adjusting a series of related algorithms depending partly on the signals by the processer to provide more accurate and reliable data that is the basis of desirable treatment plans, and sending corresponding instructions by the processer for automatic operations of the artificial pancreas to realize a closed loop control.

16 Claims, 5 Drawing Sheets

(51) Int. Cl.
    *A61M 5/142*       (2006.01)
    *A61B 5/145*       (2006.01)
    *A61B 5/00*         (2006.01)
    *A61B 5/0205*     (2006.01)
    *A61B 5/11*         (2006.01)

(52) U.S. Cl.
    CPC ........ A61M 5/14248 (2013.01); G16H 40/63 (2018.01); *A61B 5/0024* (2013.01); *A61B 2560/0214* (2013.01); *A61B 2560/0462* (2013.01); *A61M 2005/1726* (2013.01); *A61M 2205/18* (2013.01); *A61M 2205/3303* (2013.01); *A61M 2205/3569* (2013.01); *A61M 2205/50* (2013.01); *A61M 2230/201* (2013.01); *A61M 2230/63* (2013.01)

(56) References Cited

U.S. PATENT DOCUMENTS

| | | | | |
|---|---|---|---|---|
| 8,423,113 | B2* | 4/2013 | Shariati | A61B 5/742 600/347 |
| 10,195,343 | B2* | 2/2019 | Kamen | A61M 5/1723 |
| 2007/0255122 | A1 | 11/2007 | Vol et al. | |
| 2010/0042043 | A1* | 2/2010 | Krijnsen | A61M 5/1723 713/324 |
| 2014/0012117 | A1* | 1/2014 | Mensinger | A61B 5/742 600/365 |
| 2014/0276419 | A1* | 9/2014 | Rosinko | A61M 5/1723 604/151 |
| 2016/0136357 | A1* | 5/2016 | Yang | A61B 5/14503 604/66 |

\* cited by examiner

SYSTEM AND METHOD FOR A CLOSED LOOP CONTROL IN AN ARTIFICIAL PANCREAS

CROSS-REFERENCE TO RELATED APPLICATION

This application is a 371 application of an international PCT application serial no. PCT/CN2016/113690, filed on Dec. 30, 2016. The entirety of the above-mentioned patent application is hereby incorporated by reference herein and made a part of this specification.

TECHNICAL FIELD

This invention generally relates to medical appliance, and more specifically to a system and method for adjustment of blood glucose related algorithm in a close loop artificial pancreas.

BACKGROUND

For a normal healthy person, the pancreas produces and releases insulin into the blood stream in response to elevated blood glucose levels. β-cells, which reside in the pancreas, produce and secrete the insulin into the blood stream, as it is needed. If β-cells become incapacitated or die, a condition known as Type I diabetes mellitus, or in some cases if β-cells produce insufficient quantities of insulin, Type II diabetes, then insulin must be provided to the body of the patient from another source.

Traditionally, since insulin cannot be taken orally, insulin has been injected with a syringe. More recently, use of infusion pump therapy has been increasing, especially for delivering insulin for diabetics. For example, external infusion pumps are worn on a belt, in a pocket, or patched to the body of the patient directly, and deliver insulin into the body via an infusion tube with a percutaneous needle or a cannula placed in the subcutaneous tissue. The medicine that is delivered by the infusion pump device can depend on the condition of the patient and the desired treatment plan. However, current insulin pumps and other diabetes treatment instruments are limited in switching between different treatment plans based on different conditions of the patient.

Desired treatment plans using a closed loop algorithm depend on accurate determination of the physical conditions of the patient, especially for the continuously glucose monitoring in tissue fluid whose concentration is easily influenced by the actions of the patient. If a patient is in sleep, due to less activity taking place in the muscle and organs than the normal state, whether she or he needs a low suspend or predictive low suspend requires to be recalculated by adjusted algorithms. Furthermore, some low-priority alerts should be muted to prevent disturbing the patient from sleep. Similarly, if a patient is doing physical exercise, her or his interstitial glucose value sensed by the glucose sensor may fluctuate sharply because of the frequent changes in the tissue fluid, but her or his glucose level should not be determined as abnormal. To realize the closed loop algorithm in an artificial pancreas, the combination of sensing the activity level of the patient and adjusting related algorithms is crucial.

SUMMARY OF THE INVENTION

To overcome the deficiencies of the prior art, one purpose of the present invention is to provide a method to realize a closed loop control in an artificial pancreas, comprising, sensing an activity level of a patient and providing signals indicative of the activity level by at least one motion sensor to at least one processer;

determining the physical state of the patient according to the activity level and adjusting a plurality of algorithms via the processer depending partly on the signals from the motion sensor, and sending corresponding instructions via the processer based on the adjusted algorithms for automatic operations to realize the closed loop control.

Alternatively, the motion sensor comprises one or more from an accelerometer, a gyroscope and an attitude sensor.

Alternatively, the method further comprises adjusting the algorithms according to different exercise intensities when the patient is in a physical exercise state.

Alternatively, the blood glucose related algorithms comprise a low-suspend algorithm, a predictive low-suspend algorithm, and an alert threshold algorithm.

Alternatively, the method further comprises automatically switching the closed loop artificial pancreas between different operation modes based at least partly on the adjusted algorithms.

Alternatively, the method further comprises automatically adjusting the insulin delivery of a basal rate mode of the closed loop artificial pancreas based at least partly on the adjusted algorithms.

Alternatively, the method further comprises automatically switching the closed loop artificial pancreas to an audio-off mode for low-priority alerts that do not require immediate action according to the adjusted algorithms.

The other purpose of the present invention is to provide a closed loop artificial pancreas using the method identified above, comprising, a patch pump and a continuous glucose monitoring (CGM) system;

at least one motion sensor set in any component of artificial pancreas, configured to sense the activity levels of a patient and provide corresponding signals;

at least one processor set in any component of artificial pancreas, configured to determine the physical states of the patient, adjust related algorithms and send corresponding instructions based partly on the signals.

Alternatively, the closed loop artificial pancreas further comprises a handset;

at least one motion sensor is set in the patch pump, the CGM system or the handset, configured to sense the activity levels of a patient and provide corresponding signals;

at least one processor is set in the patch pump, the CGM system or the handset, configured to determine the physical states of the patient, adjust related algorithms and send corresponding instructions based partly on the signals.

Alternatively, the patch pump and the CGM system are separated from each other; at least one motion sensor is set in the patch pump or the CGM system, and two processers are set in the patch pump and the CGM system respectively.

Alternatively, the patch pump and the CGM system are integrated in a single-needle-integrated artificial pancreas in which both a motion sensor and a processor are set.

The present invention has advantages in the following ways: Firstly, applying the motion sensors in the close loop artificial pancreas enables a comprehensive grasp of the patient's activity levels for a more rational treatment by distinguishing sleep and physical exercise states from the normal state; secondly, adjusting blood glucose related algorithms according to different activity levels and exercise intensities of the patient provides more applicable data and enables automatic operations of the artificial pancreas, such as suspending the delivery under low glucose condition, switching between different operation modes and adjusting insulin delivery of specific operation mode, which reflect the advantages of the closed loop control of artificial pancreas in an all-round way; thirdly, muting some low-priority alerts when sensing the patient in the state of sleep or physical exercise can reduce unnecessary disturbance to the patient making the system more pleasant to use. To sum up, the application of motion sensors in the close loop artificial pancreas enables algorithm adjustments based on different physical states and exercise intensities of the patient to provide more accurate and reliable blood glucose related data that is the basis of desirable treatment plans, and a closed loop artificial pancreas using this method satisfies the requirements of the patient on safety and intelligence of a diabetes treatment system in a more sophisticated way.

DETAILED DESCRIPTION

To make the above-mentioned objects, features and advantages of the present invention more obvious and understandable, the embodiments of the present invention are described in the following through specific embodiments.

Figure 1:
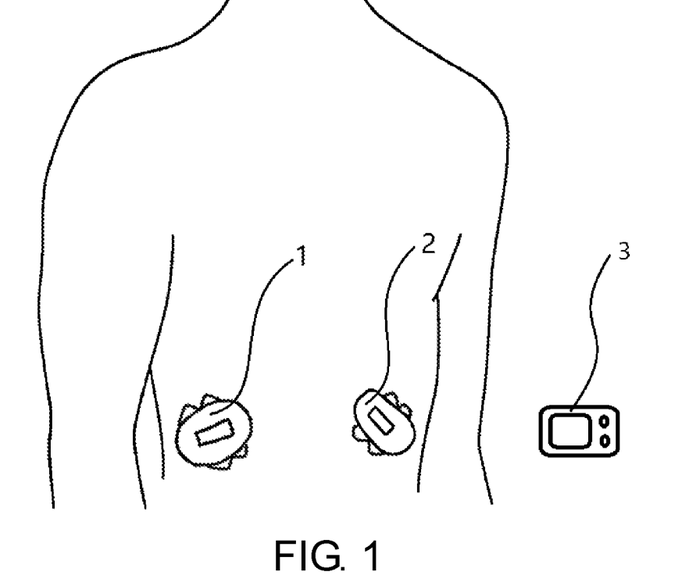
FIG. 1-3 are schematic diagrams of a patient wearing an artificial pancreas in the present invention.

Referring to FIG. 1, an embodiment of the system using the closed loop control in the present invention is provided. FIG. 1 illustrates a patient wearing a CGM system 1 configured to monitor the blood glucose changes in real time and a patch pump 2 configured to deliver insulin to the patient, both equipped with a processor, which communicates with each other via a processor set in a portable handset 3 configured to receive signals, process and display data, and send instructions. At least one motion sensor is set in any one, or two, or all three of the CGM system 1, the patch pump 2 and the handset 3, which will be described in following paragraphs.

Figure 2:
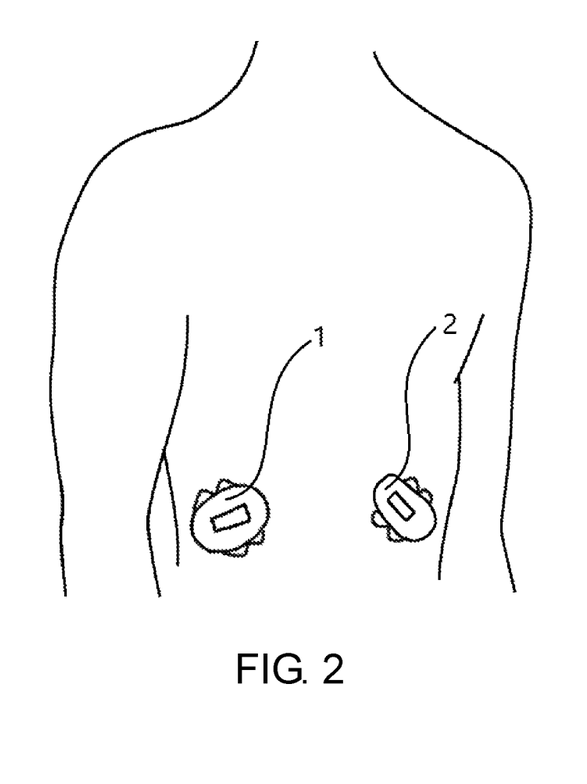

Referring to FIG. 2, an embodiment of the system using the closed loop control in the present invention is provided. FIG. 2 illustrates a patient wearing an artificial pancreas comprising two separate components: a CGM system 1 and a patch pump 2, which communicate with each other via their respective processors. At least one motion sensor is set in the CGM system 1 and/or the patch pump 2, which will be described in following paragraphs.

Figure 3:
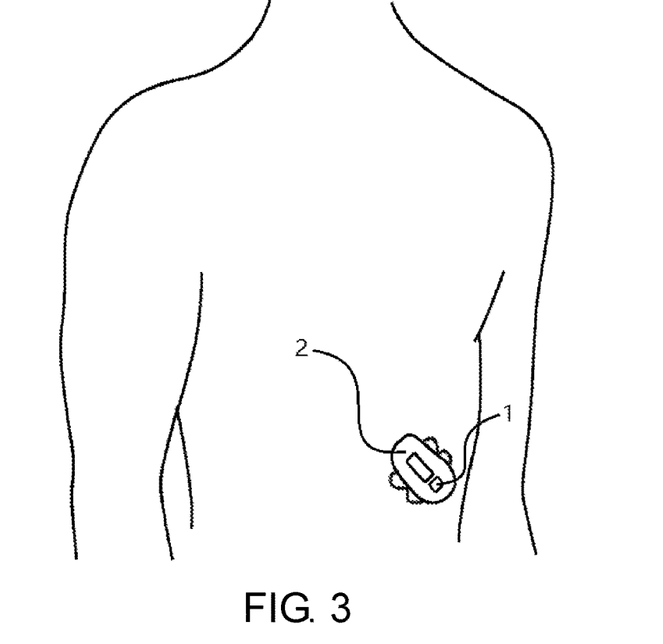

Referring to FIG. 3, an embodiment of the system using the closed loop control in the present invention is provided. FIG. 3 illustrates a patient wearing a single-needle-integrated artificial pancreas integrated by a patch pump 2 and a built-in CGM system 1. A processor is set in the single-needle-integrated artificial pancreas to perform all the functions including receiving signals, processing data, and sending instructions. A motion sensor is also set in the single-needle-integrated artificial pancreas.

Figure 4:
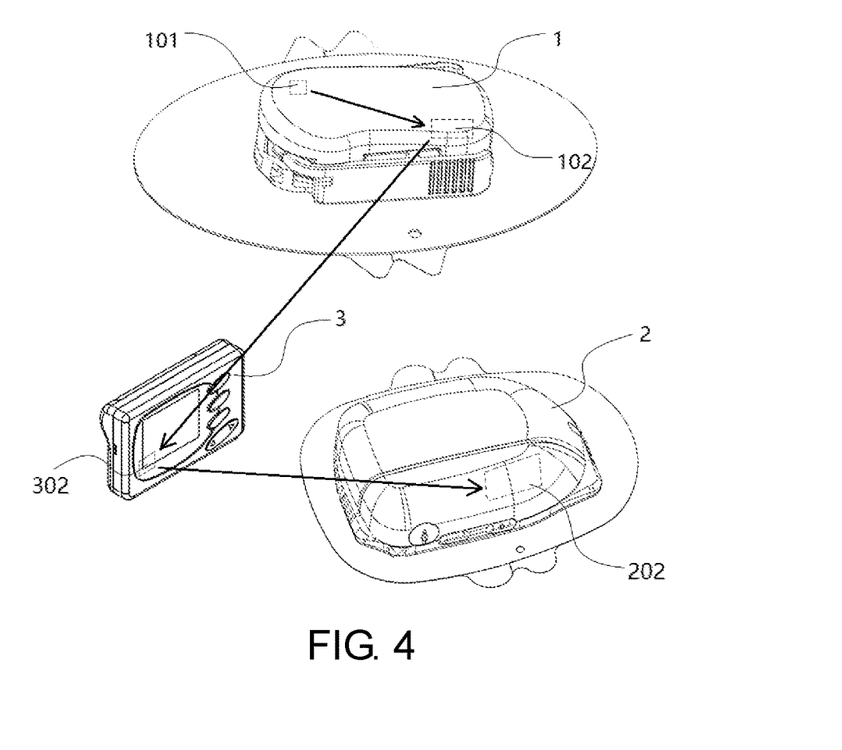
FIG. 4-9 are schematic diagrams of representative method in the embodiments of the present invention.

Referring to FIG. 1 and FIG. 4, an embodiment of the present invention is provided. As shown in FIG. 4, a motion sensor 101 is set in the CGM system 1, configured to sense activity levels of the patient and send corresponding signals. A processor 102 in the CGM system 1 receives signals from the motion sensor 101 and adjusts related algorithms depending partly on the signals, and the data processed using the adjusted algorithms is sent to a processor 302 in a handset 3. Through further processing, the processor 302 determines whether an operation of the patch pump 2 is needed. If so, the processor 302 sends an instruction to the processor 202 of the patch pump 2 to perform the corresponding operation automatically.

In this embodiment, the motion sensor 101 is a three-axis accelerometer 101.

When the patient is in physical exercise, the start and end of the exercise, as well as the intensity of the exercise can be determined by the equation:

$$ACC_{power} = \sqrt{ACC_X^2 + ACC_Y^2 + ACC_Z^2}$$

Where, $ACC_{power}$ is the acceleration amplitude of all three axes;
$ACC_X$ is the acceleration data of the X axis;
$ACC_Y$ is the acceleration data of the Y axis;
$ACC_Z$ is the acceleration data of the Z axis.

The attitudes of the patient, whether she or he is standing, sitting, lying, or changing from one of these attitudes to another, can be sensed by the three-axis accelerometer 101. In other words, the attitude changes of the patient can be tracked by the three-axis accelerometer 101 in real time. When the patient goes to sleep, the state can be determined by the equation:

$$ACC_{var} = (ACC_X - ACC_{X|PRE})^2 + (ACC_Y - ACC_{Y|PRE})^2 + (ACC_Z - ACC_{Z|PRE})^2$$

Where, $ACC_{var}$ is the acceleration variation of all three axes;
$ACC_X$ is the acceleration data of the X axis;
$ACC_Y$ is the acceleration data of the Y axis;
$ACC_Z$ is the acceleration data of the Z axis;
$ACC_{X|PRE}$ is the acceleration data of the X axis at a previous time;
$ACC_{Y|PRE}$ is the acceleration data of the Y axis at a previous time;
$ACC_{Z|PRE}$ is the acceleration data of the Z axis at a previous time.

The algorithms adjusted by the processor 102 comprise but not limited to a low-suspend algorithm, a predictive low-suspend algorithm; and an alert threshold algorithm. As shown in FIG. 4, data processed according to the adjusted algorithms is sent to the handset 3, and the processor 302 in the handset 3 determines whether an operation should be performed automatically by the patch pump 2. If so, the processor 302 sends an instruction to the processor 202 of the patch pump 2. The operations comprise but not limited to a delivery suspend according to the low-suspend algorithm or the predictive low-suspend algorithm, a change of operation modes, an adjustment of the insulin delivery amount of a basal rate mode, and switching the CGM system 1 and the patch pump 2 into an audio-off mode for low priority alerts according to the adjusted algorithm when the patient is determined in a state of sleep or physical exercise.

Figure 5:
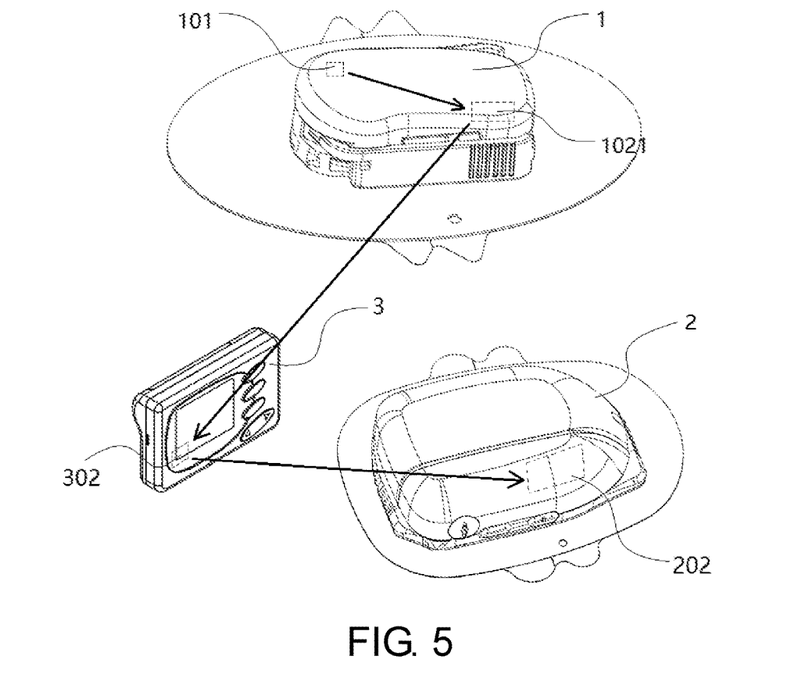

Referring to FIG. 1 and FIG. 5, an embodiment of the present invention is provided. As shown in FIG. 5, a motion sensor 101 is set in the CGM system 1, and the signals provided by the motion sensor 101 are sent to and processed by a processor 302 set in the handset 3 via a transmitting module 1021 set in the CGM system 1. The processor 302 in the handset 3 adjusts related algorithms depending partly on the signals, and determines whether an operation of the patch pump 2 is needed. If so, the processor 302 sends an instruction to the processor 202 of the patch pump 2 to perform the corresponding operation automatically.

Figure 6:
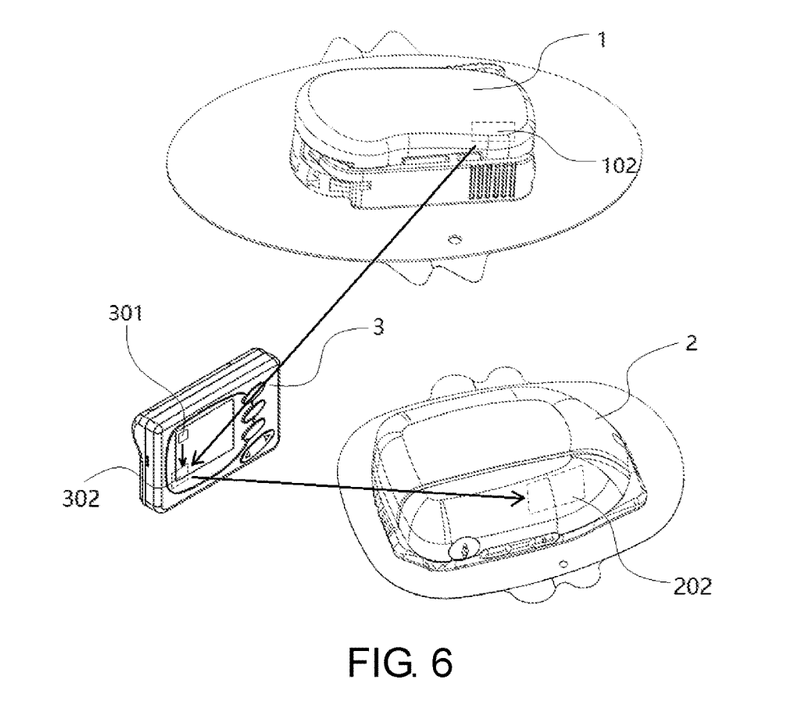

Referring to FIG. 1 and FIG. 6, an embodiment of the present invention is provided. As shown in FIG. 6, a motion sensor 301 is set in a portable handset 3 to sense the activity levels of the patient when the patient is carrying the handset 3, and the signals provided by the motion sensor 301 are sent to and processed by a processer 302 set in the handset 3. The processer 302 in the handset 3 adjusts related algorithms depending partly on the signals, and processes the glucose data provided by a processer 102 of the CGM system 1 accordingly. The processer 302 in the handset 3 further determines whether an operation of the patch pump 2 is needed. If so, the processer 302 of the handset 3 sends an instruction to the processer 202 of the patch pump 2 to perform the corresponding operation automatically.

Figure 7:
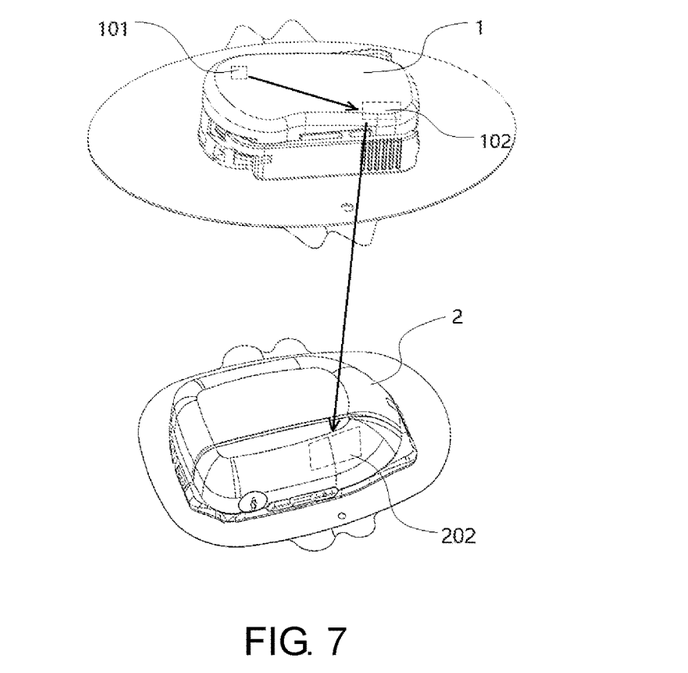

Referring to FIG. 2 and FIG. 7, an embodiment of the present invention is provided. As shown in FIG. 7, a motion sensor 101 is set in the CGM system 1, and the signals provided by the motion sensor 101 are sent to and processed by a processer 102 which is also set in the CGM system 1. The processer 102 adjusts related algorithms depending partly on the signals, and the data processed using the adjusted algorithm is sent to a processer 202 in a patch pump 2 directly. Through further processing, the processer 202 determines whether an operation of the patch pump 2 is needed. If so, an instruction is generated from the processer 202 for the patch pump 2 to perform the corresponding operation automatically.

Figure 8:
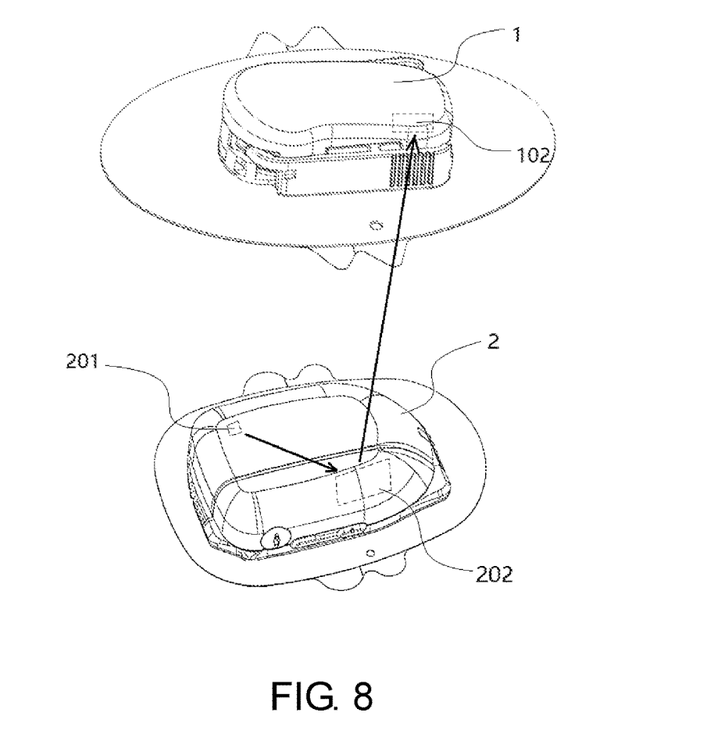

Referring to FIG. 2 and FIG. 8, an embodiment of the present invention is provided. As shown in FIG. 8, a motion sensor 201 is set in the patch pump 2, and the signals provided by the motion sensor 201 are sent to the processer 202 which is also set in the patch pump 2. The processer 202 determines the physical state of the patient, in specific, whether the patient is in sleep or doing physical exercise, then switches the patch pump 2 to an appropriate operation mode according to the state of the patient automatically. At the same time, the processer 202 sends a signal comprising the physical state and exercise intensity of the patient to the processer 102 of the CGM system to adjust related algorithms, calculating the blood glucose values based on the adjusted algorithms which reflect the actual state of the patient.

Figure 9:
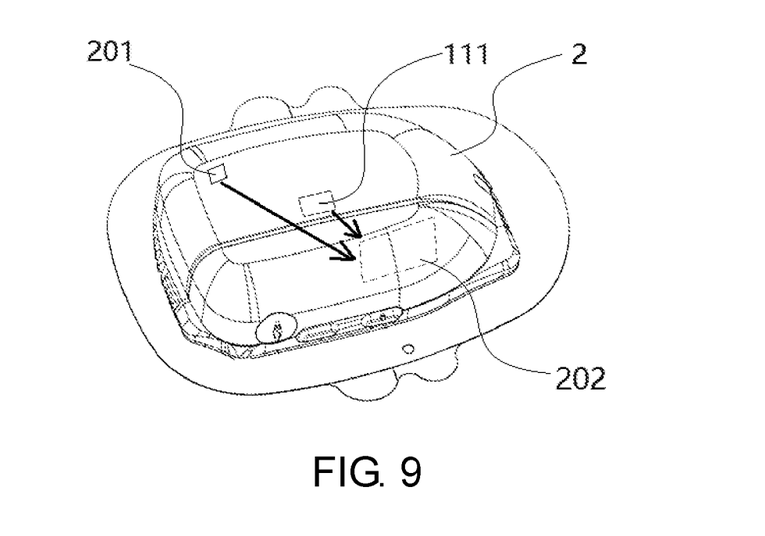

Referring to FIG. 3 and FIG. 9, an embodiment of the present invention is provided. As shown in FIG. 9, a single-needle-integrated artificial pancreas comprises a patch pump 2 and a built-in glucose sensor 111 in FIG. 9. A motion sensor 201 is set in the single-needle-integrated artificial pancreas, and a processer 202 configured to perform all the functions of receiving signals, processing data, and sending instructions is also set in the single-needle-integrated artificial pancreas. The motion sensor 201 senses activity levels of the patient and send corresponding signals to the processer 202. The processer 202 receives signals from the motion sensor 201 and adjusts related algorithms depending partly on the signals to process the glucose data received from the built-in glucose sensor 111, and determines whether an operation of the single-needle-integrated artificial pancreas is needed. If so, an instruction is generated from the processer 202 for the patch pump 2 to perform the corresponding operation automatically, realizing the closed loop control in the single-needle-integrated artificial pancreas.

The above descriptions of the detailed embodiments are only to illustrate the principle and the effect of the present invention, and it is not to limit the scope of the present invention. Those skilled in the art can modify or change the embodiments without departing from the spirit and scope of the present invention. Accordingly, all equivalent modifications and variations completed by persons of ordinary skill in the art, without departing from the spirit and technical idea of the present invention, should fall within the scope of the present disclosure defined by the appended claims.

The invention claimed is:

1. A method to realize a closed loop control in an artificial pancreas, wherein the artificial pancreas comprises a patch pump, and a continuous glucose monitoring (CGM) system, the method comprising:
   sensing an activity level of a patient by a motion sensor set in the CGM system;
   providing signals indicative of the activity level of the patient under specific attitudes by the motion sensor to a processer set in the CGM system of the artificial pancreas, wherein the specific attitudes include standing, sitting, lying, or changing from one of the specific attitudes to another;
   determining the physical state of the patient according to the activity level via the processer set in the CGM system;
   adjusting a plurality of algorithms via the processer set in the CGM system depending partly on the signals from the motion sensor; and
   sending corresponding instructions based on the adjusted algorithms to a processor set in the patch pump from the processer set in the CGM system for automatic operations of the artificial pancreas;
   wherein the method further comprises automatically switching the artificial pancreas between different operation modes based at least partly on the adjusted algorithms.

2. The method according to claim 1, wherein the motion sensor comprises one or more from an accelerometer, a gyroscope and an attitude sensor.

3. The method according to claim 1, wherein the algorithms comprise a low-suspend algorithm.

4. The method according to claim 1, wherein the algorithms comprise a predicted low-suspend algorithm.

5. The method according to claim 1, wherein the algorithms comprise an alert threshold algorithm.

6. The method according to claim 1, wherein the method further comprises automatically adjusting the insulin delivery of a basal rate mode of the artificial pancreas based at least partly on the adjusted algorithms.

7. The method according to claim 1, wherein the method further comprises automatically switching the artificial pancreas to an audio-off mode for low-priority alerts that do not require immediate action according to the adjusted algorithms.

8. A closed loop artificial pancreas adapted perform the method according to claim 1, the closed loop artificial pancreas comprising,
   a patch pump and a continuous glucose monitoring (CGM) system;
   a motion sensor set in the CGM system, configured to sense the activity levels of a patient and provide corresponding signals;
   a processer set in the patch pump; and
   a processer set in the CGM system, configured to determine the physical states of the patient, adjust related algorithms and send corresponding instructions based partly on the signals to the processor set in the patch pump.

9. The closed loop artificial pancreas according to claim 8, wherein the closed loop artificial pancreas further comprises:
   a processer set in a handset carried by the patient, configured to adjust related algorithms depending partly on the signals provided by the motion sensor and send corresponding instructions based partly on the signals to the processor set in the patch pump.

10. The closed loop artificial pancreas according to claim 8, wherein
the patch pump and the CGM system are separated from each other; and
two processers are set in the patch pump and the CGM system respectively.

11. The closed loop artificial pancreas according to claim 8, wherein
the patch pump and the CGM system are integrated in a single-needle-integrated artificial pancreas; and
both a motion sensor and a processer are set in the single-needle-integrated artificial pancreas.

12. The method according to claim 1, wherein the method further comprises adjusting the algorithms according to different exercise intensities when the patient is in a physical exercise state.

13. A method to realize a closed loop control in an artificial pancreas, wherein the artificial pancreas comprises a patch pump, and a continuous glucose monitoring (CGM) system, the method comprising:
sensing an activity level of a patient by a motion sensor set in the patch pump;
providing signals indicative of the activity level of the patient under specific attitudes by the motion sensor to a processer set in the patch pump of the artificial pancreas, wherein the specific attitudes include standing, sitting, lying, or changing from one of the specific attitudes to another;
determining the physical state of the patient according to the activity level via the processer set in the patch pump;
sending signals corresponding the physical state of the patient to a processor set in the CGM system via the processer set in the patch pump;
adjusting a plurality of algorithms via the processer set in the CGM system; and
calculating blood glucose values based on the adjusted algorithms via the processer set in the CGM system for automatic operations of the artificial pancreas;
wherein the method further comprises automatically switching the artificial pancreas between different operation modes based at least partly on the adjusted algorithms.

14. A closed loop artificial pancreas adapted perform the method according to claim 13, the closed loop artificial pancreas comprising,
a patch pump and a continuous glucose monitoring (CGM) system;
a motion sensor set in the patch pump, configured to sense the activity levels of a patient and provide corresponding signals;
a processer set in the CGM system; and
a processer set in the patch pump, configured to determine the physical states of the patient, and send signals corresponding the physical state of the patient to a processor set in the CGM system;
wherein the processer set in the CGM system is configured to adjust related algorithms, and calculate blood glucose values based on the adjusted algorithms for automatic operations of the artificial pancreas.

15. A method to realize a closed loop control in an artificial pancreas, wherein the artificial pancreas comprises a patch pump, and a continuous glucose monitoring (CGM) system, the method comprising:
sensing an activity level of a patient by a motion sensor set in a handset;
providing signals indicative of the activity level of the patient under specific attitudes by the motion sensor to a processer set in the handset, wherein the specific attitudes include standing, sitting, lying, or changing from one of the specific attitudes to another;
determining the physical state of the patient according to the activity level via the processer set in the handset;
sending signals corresponding the physical state of the patient to a processor set in the handset;
adjusting a plurality of algorithms via the processer set in the handset, and processing glucose data provided by a processer set in the CGM system; and
sending corresponding instructions based on the adjusted algorithms to a processer set in the patch pump from the processer set in the handset for automatic operations of the artificial pancreas;
wherein the method further comprises automatically switching the artificial pancreas between different operation modes based at least partly on the adjusted algorithms.

16. A closed loop artificial pancreas adapted perform the method according to claim 15, the closed loop artificial pancreas comprising,
a patch pump and a continuous glucose monitoring (CGM) system;
a processer set in the patch pump; and
a processer set in the CGM system, configured to provide the glucose data;
wherein a handset is carried by the patient, and the handset have a motion sensor and a processor;
wherein the motion sensor set in handset is configured to sense the activity levels of a patient and provide corresponding signals;
wherein the processer set in a handset is configured to determine the physical states of the patient, adjust related algorithms, process the glucose data provided by a processer set in the CGM system and send corresponding instructions based partly on the signals to the processor set in the patch pump.

* * * * *